United States Patent [19]

Badger et al.

[11] Patent Number: 4,638,436
[45] Date of Patent: Jan. 20, 1987

[54] TEMPERATURE CONTROL AND ANALYSIS SYSTEM FOR HYPERTHERMIA TREATMENT

[75] Inventors: Christopher W. Badger; Everette C. Burdette, both of Champaign, Ill.; Steven C. Leech, Tinton Falls, N.J.; John F. McCarthy, Champaign, Ill.

[73] Assignee: Labthermics Technologies, Inc., Champaign, Ill.

[21] Appl. No.: 654,603

[22] Filed: Sep. 24, 1984

[51] Int. Cl.$^4$ .................. G06F 15/42; A61F 7/00; A61N 1/08
[52] U.S. Cl. ........................... 364/414; 128/401; 128/736; 128/804
[58] Field of Search ............... 364/413, 414, 415; 128/399, 401, 736, 783, 804; 374/121

[56] References Cited

U.S. PATENT DOCUMENTS

| 4,190,053 | 2/1980 | Sterzer | 128/399 |
|---|---|---|---|
| 4,204,549 | 12/1977 | Paglione | 128/784 |
| 4,246,784 | 6/1979 | Bowen | 374/117 |
| 4,249,539 | 2/1979 | Vilkomerson et al. | 128/660 |
| 4,390,025 | 4/1981 | Takemura et al. | 128/660 |
| 4,397,314 | 8/1983 | Vaguine | 128/399 |
| 4,416,552 | 10/1981 | Hessemer, Jr. et al. | 374/117 |
| 4,445,516 | 5/1981 | Wollnik et al. | 128/736 |
| 4,513,749 | 11/1982 | Kino et al. | 128/660 |
| 4,513,750 | 2/1984 | Heyman et al. | 128/660 |
| 4,589,423 | 5/1986 | Turner | 128/804 |

OTHER PUBLICATIONS

Astra 200 ™ Publication of Orcotherm Corporation.
Vaguine, V. A., "Physics and Performance of Clini--Therm's Hyperthermia Systems with Multiple Heating Modalities", publication of Clini-Therm Corporation, May 1984.
HLI 500 Hyperthermia System, publication of Societe de Equipments Medicaux s.a.r.l., Jun. 1980.
BSD-300 Mobile Hyperthermia System, publication of BSD Medical Corp.
BSD-1000 Hyperthermia System, publication of BSD Medical Corp.
"Modular Approach Provides Easy Expansion of Hyperthermia Treatment Capability", publication of Clini--Therm Corp., Oct. 1982.
Sapareto, S. A., et al., "Thermal Dose Determination in Cancer Therapy", *Int. J. Radiation Oncology Biol. Phys.*, vol. 10, No. 6, Jun. 1984, 787–800.
van den Berg, P. M., et al., "A Computational Model of the Electromagnetic Heating of Biological Tissue with Application to Hyperthermic Cancer Therapy", *IEEE Trans. Bio–Med. Engineering*, vol. BME-30, No. 12, Dec. 1983, 797–805.
Samaras, G. M., "Intracranial Microwave Hyperthermia: Heat Induction and Temperature Control", *IEEE Trans. Bio–Med. Eng.*, vol. BME-31, No. 1, Jan. 1984.
Fessenden, P., et al., "Experience with a Multitransducer Ultrasound System for Localized Hyperthermia of Deep Tissues", *IEEE Trans. Bio–Med. Eng.*, Jan. 1984, 126–135.

List Continued on next page.

Primary Examiner—Jerry Smith
Assistant Examiner—Clark A. Jablon
Attorney, Agent, or Firm—Niro, Scavone, Haller & Niro, Ltd.

[57] ABSTRACT

A system for controlling a hyperthermia treatment device having energy applicators for heating a portion of a patient's body to attain a predetermined temperature protocol for therapeutic treatment of patient tumors. The system monitors energy application and displays a video presentation of correlative temperature data to an operator who responds by adjusting the energy application to achieve the desired treatment protocol. The system further accumulates a hyperthermia treatment data base, and predetermined temperature protocols for the patient are prepared by comparison with data base protocols for similar tumor conditions. Various figures of merit are also determined and stored in the data base and ongoing treatments are comparerd with the data base to characterize the most effective treatment protocol.

46 Claims, 8 Drawing Figures

Microfiche Appendix Included
(1 Microfiche, 48 Pages)

OTHER PUBLICATIONS

Dickinson, R. J., "An Ultrasound System for Local Hyperthermia using Scanned Focused Transducers", *IEEE Trans. Bio-Med. Eng.*, vol. BME-31, No. 1, Jan. 1984, 120–125.

Strohbehn, J. W., "A Survey of Computer Simulations of Hyperthermia Treatments", *IEEE Trans. Bio-Med. Eng.*, vol. BME-31, No. 1, Jan. 1984, 136–149.

Divrik, A. M., et al., "Inference of Complete Tissue Temperature Fields from a Few Measured Temperatures: An Unconstrained Optimization Method", *IEEE Trans. Bio-Med. Eng.*, vol. BME-31, No. 1, Jan. 1984, 150–160.

Table of Contents, *IEEE Trans. Bio-Med. Eng.*, vol. BME-31, No. 1, Jan. 1984.

Vaguine, V. A., et al. "Multiple Sensor Optical Thermometry System for Application in Clinical Hyperthermia", *IEEE Trans. Bio-Med. Eng.*, vol. BME-31, No. 1, Jan. 1984, 168–172.

TEMPERATURE CONTROL AND ANALYSIS SYSTEM FOR HYPERTHERMIA TREATMENT

A computer software routine is included as part of this Specification as a microfiche Appendix having one microfiche page of forty-eight frames.

The present invention relates generally to an apparatus and method for control of a hyperthermia patient treatment protocol. More particularly the invention relates to a novel apparatus and method for controlling a hyperthermia treatment device by real time operator adjustment of energy input to portions of the patient's body after operator evaluation of the video presentation of correlative temperature data from treated portions of the patient's body. The invention is further related to the accumulation of a hyperthermia treatment data base and for assessing relative figures of merit for different hyperthermia treatment protocols.

Hyperthermia treatment of cancerous tumors is a relatively new method of destruction of cancerous growths within a patient's body. Various systems have been developed to selectively heat the cancerous growths by using electromagnetic radiation and more recently by using ultrasound energy. In order to attain optimum effectiveness in hyperthermia treatment, the apparatus should be able to characterize and to document the temperature distribution associated with the tumor itself and with normal tissue surrounding the tumor. Furthermore, it is desirable to have the ability to display to the operator in the most effective manner the ongoing thermal treatment to enable optimization of the treatment to attain a predetermined temperature protocol. Previous apparatus and methods for hyperthermia treatment have attempted to characterize the thermal treatment by displaying tables of tumor location, temperature and time of treatment or alternatively by displaying plots of the temperature versus time of treatment for the temperature sensors. The association of each of the sensors with a particular time-temperature plot has been accomplished by color coding of the line of the plot to the associated temperature sensor. (See, for example, the brochure entitled "BSD-200", BSD Medical Corporation, Salt Lake, Utah). Prior hyperthermia apparati have also generally utilized only a single one of a plurality of temperature sensors to provide a feedback signal to control the temperature of the entire tumor (see, for example, brochures entitled, "Astra 200", Oncotherm, Inc., Los Angeles, Calif.; and, the brochure entitled, "Modular Approach Provides Easy Expansion of Hyperthermia Capability"; from Clini-Therm Corp., Dallas, Tex.).

BRIEF SUMMARY OF THE INVENTION

A primary object of the invention is to provide an improved apparatus and method for control of a hyperthermia patient treatment device.

A more particular object of the invention is to provide a novel apparatus and method for real time operator control of hyperthermia treatment using a video presentation of correlative temperature data and applied energy for treated portions of the patient's body.

Another object of the invention is to provide an improved apparatus and method for accumulation of a data base of patient treatment history for a variety of locations, sizes and types of tumors.

A further object of the invention is to provide a novel apparatus and method for generating video presentations of a plurality of topographical maps of isothermal temperatures for different depths in the vicinity of a tumor in a patient's body.

An additional object of the invention is to provide an improved method and apparatus for preparing predetermined hyperthermia treatment protocols and for adapting an ongoing treatment using a hyperthermia treatment data base accumulated by controlling the treatment using a video presentation of correlative temperature data and applied energy for treated portions of a patient's body.

Another object of the invention is to provide a novel apparatus and method for preparing a predetermined hyperthermia treatment protocol for a tumor in a patient's body by mapping data in a hyperthermia treatment data base to identify tumor characteristics similar to the patient's tumor and modifying the data base protocol to develop the predetermined protocol.

A further object of the invention is to provide an improved apparatus and method for determining a figure of merit for a hyperthermia treatment to enable characterization of therapeutic results of the treatment and to allow real time modification of an ongoing treatment to improve the therapeutic results.

Further objects and advantages of the present invention, together with the organization and manner of operation thereof, will become apparent from the following description of the invention when taken in conjunction with the accompanying drawings wherein like reference numerals designate like components throughout the several figures.

DETAILED DESCRIPTION

Broadly stated the present invention is a system which cooperates with an operator to control a hyperthermia patient treatment device by using a video display presentation of correlative temperature data from the region of the patient's body undergoing treatment to enable the operator to adjust energy input to optimize treatment conditions. The video presentation includes a prompt signal from a computer to request operator consideration of whether adjustment of the energy input is necessary to achieve a predetermined time-temperature protocol. Alternatively, the system can operate in an automatic mode with operator interaction limited to emergency intervention and monitoring of the treatment protocol.

The correlative temperature data includes a display on a grid of the spatial location of color coded temperature sensors with respect to the displayed tumor outline which has been calculated from information input by the operator. The correlative temperature data further includes a second display of the same grid area as the sensor location grid but shows the energy input power level in each of a plurality of subelements of the grid. An accompanying display illustrates by a color coded bar graph the temperature level for each of the plurality of temperature sensors. The bar graph temperature display is separated into two groups with one group associated with temperatures in the normal tissue and another group associated with temperatures in the treatment or therapeutic region of the tumor.

A color coded scale is preferably positioned between the two groups of bar graphs. The color coded scale for the normal tissue region is divided into two color zones, a substantially safe zone and a substantially harmful zone. The color coded scale for the tumor region is divided into three color zones, including a lower zone, a preferred treatment zone and an upper zone.

An additional real time display of correlative temperature data includes maximum and minimum temperatures reached as a function of treatment time among all temperature sensors within each of the two groups of sensors in the tumor and in the normal tissue regions. This information is also stored in memory, and the thermal treatment history is documented by storing the correlative temperature data, the applied energy data and various characteristic features of the data, such as figures of merit. This thermal history information can be used in real time to modify the treatment to achieve the optimum results. After patient treatment the information can be compared in light of the therapeutic results to enable preparation of future predetermined treatment protocols. This thermal treatment history can be further utilized and examined by generating topographical displays of isothermal regions in the vicinity of the tumor. A data base of the patient treatment history and therapeutic results is also accumulated for use in treatment of other patients.

Figure 1:
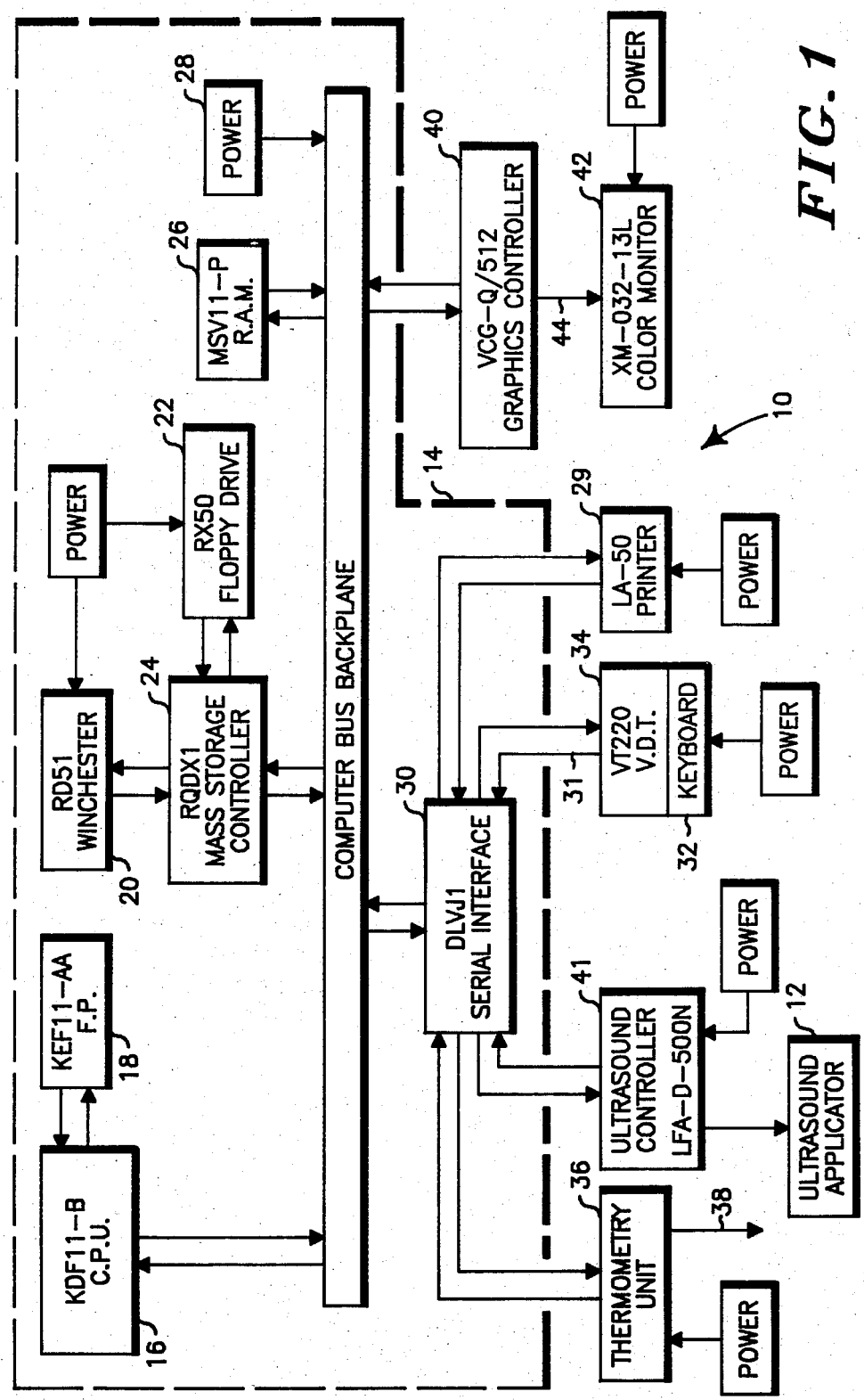
FIG. 1 is a block diagram of an apparatus for hyperthermia treatment of patient tumors under control of an operator.

Referring now to the drawings and in particular to FIG. 1, a block diagram of hardware for a system constructed in accordance with one embodiment of the present invention is indicated generally at 10. The following model numbers of products and equipment represent preferred components although other similar components can be substituted. The hardware 10 includes an applicator means for applying energy to heat portions of the patient's body. The applicator means in the illustrated embodiment is an ultrasound applicator 12 which generates ultrasonic wave energy by applying a high voltage radio frequency (RF) signal to one side of a piezoelectric crystal grounded on a second side of the crystal. The crystal is modulated by the RF signal to generate ultrasonic waves which are applied to selected areas of the patient's body. In other embodiments of the invention other types of energy, such as microwaves, can be used to heat the patient's body. The applicator 12 is actuated responsive to commands received from computer means, such as a computer 14. In the illustrated embodiment the computer 14 is a Micro-PDP 11 (a trademark of Digital Equipment Corporation) manufactured by Digital Equipment Corporation, Nashua, N.H. As shown in FIG. 1 the computer 14 includes a number of components, each of which are manufactured by Digital Equipment Corp. The computer 14 includes a KDF11-B central processing unit 16 and a coupled floating point integrated circuit chip 18, KEF11-AA. The computer 14 includes storage means, such as an RD51 Winchester drive mass storage unit 20 with 10 megabytes storage and an RX50 floppy disk storage unit 22. Both the Winchester storage unit 20 and the floppy disk storage unit 22 are controlled by an RQDX1 mass storage controller 24. The computer 14 also includes a random access memory 26 (RAM), which in the illustrated embodiment is a MSV11-P having 256 kilobytes of storage. Power for the computer 14 is supplied by an H7864 power supply 28. Input/output is accomplished through an interface 30, such as, for example, a DLVJ1 which is a four line asynchronous serial interface, and in the illustrated embodiment is an integral component supplied with the PDP-11. The computer 14 implements a temperature treatment regimen or protocol in accordance with appropriate protocol data and instructions stored in the floppy disk storage unit 22 or in the Winchester storage unit 20. In a preferred embodiment the data and instructions are loaded from the Winchester storage unit 20 into the RAM 26, and the computer executes a hyperthermia treatment protocol characterized by the data and instructions stored in the RAM 26. The slower loading floppy disk storage unit 22 is preferably used after completion of the protocol for permanent storage of the measured data from the hyperthermia treatment.

The operator interacts with the computer 14 through operator means to supply an operator signal 31 to the computer 14 responsive to an operator input. In the illustrated embodiment, the operator means is a keyboard 32 in FIG. 1, which is part of a video display terminal 34 (for example, a VT 220 from Digital Equipment Corp). The operator input, or manipulation, is therefore the depression of the keyboard keys, and the keyboard 32 generates the operator signal 31 to the computer 14. In another form of the invention the operator means can be a remote interaction device, such as a personal computer-keyboard and/or display keyboard system (not shown) allowing remote monitoring and control of the treatments. For example, a physician could control implementation of various hyperthermia treatments at a plurality of locations remote from the physician's office.

The ultrasound energy input by the applicator 12 to the treatment area results in an increase in temperature of the treatment area. This change in temperature is detected by a thermometry unit 36, and in a preferred embodiment the thermometry unit 36 is a multi channel system coupled to temperature sensing means, such as copper-constantan thermocouple temperature sensors 38 disposed within the patient's body. The sensors 38 preferably are contained within plastic catheters which are placed in the patient's body, and the catheter is withdrawn before treatment in order to avoid disruption of the ultrasound heating pattern. Alternatively, hypodermic needles containing thermocouples can be inserted into the patient's body. If operating using the microwave energy to heat the patient's body, the needles should be withdrawn to avoid complete disruption of the desired heating pattern. A plurality of the sensors 38 can be disposed within one of the catheters (or if appropriate, the hypodermic syringes) enabling placement of a plurality of the sensors 38 along a selected line in the patient's body. In other forms of the invention, the temperature sensing means can be thermistors or other suitable temperature sensing devices.

In preparation for performance of the hyperthermia treatment, the operator establishes initial treatment conditions by activating the executive program which invokes the data entry program and guides the operator through the necessary steps for treatment startup. The operator enters, for example, patient history, length of time of treatment and desired temperature threshold values for the predetermined temperature protocol. This startup information can be stored for later recall and initiation of treatment, or the operator can immediately commence the treatment procedure. In addition, the operator enters further information, such as the location of the temperature sensors 38 and whether the sensor 38 is in the tumor region or the normal tissue region. A separate computer program generates an outline of the tumor region, and the operator is able to choose to enter fictitious temperature sensors to change the outline or can choose to modify this outline using additional available information. Consequently, after this modification the executive program resumes and sequences the operator through the executive program providing the appropriate command requests to provide for various functionality as described in the specification. The executive program can be written in any of a plurality of languages, including, for example, assembly language, BASIC and FORTRAN; and the executive program can operate under a plurality of commercially available operating systems, such as RSTS, RT-11, iRMX-86, CP/M-86, MS-DOS or UNIX, on any of the various commercial computer systems.

In another embodiment of the invention, instead of using the executive program, all necessary functions can be provided by a plurality of separate callable software routines for the operator to call up at his option. In such case, there is no need for the executive program.

Control of the treatment temperature is critical to achieve the preselected time and temperature protocol desired for most effective patient treatment. Control of the time-temperature protocol is best accomplished by a system wherein the operator observes color coded video presentations of the type depicted in FIGS. 3-5. Display of each of the video presentations is accomplished by a graphics controller unit 40, such as, for example a VCG-Q/512 manufactured by Peritek Corporaton, Oakland, Calif. The video presentation is displayed on a video display 42, such as an XM-032-13L color monitor purchased from Grinnell Systems, Inc., San Jose, Calif. The color images are constructed by the controller unit 40 which receives a digitized video output 44 from execution of the graphics software program in a module to be discussed later. The controller unit 40 converts the digital video output to an analog video output suitable for display on the video display 42. The controller unit 40 has one hundred twenty eight kilobytes of internal memory for storage of the red, green and blue bits which describe each pixel on the video presentation. Further details of operation of a typical form of the controller unit 40 can be obtained from, "Fundamentals of Computer Graphics", J. D. Foley and A. Van Dam, Addison Wesley Co., Reading, MA, 1982, pages 112-136; and from U.S. Pat. Nos. 4,121,283; 4,139,838; and 4,213,189 which are incorporated by reference herein.

The video presentations viewed by the operator contain temperature correlative data characteristic of the treatment time and the temperature at each of the temperature sensors 38. If the temperature falls outside the desired range of the predetermined temperature protocol, the computer 14 generates a prompt signal which is displayed as an alphanumeric output on the video display terminal 34. The alphanumeric output typically takes the form of a notice that the temperature will be out of range in a brief period and asks the operator whether manipulation should be performed, such as an adjustment of the level of applied energy. The computer 14 accomplishes this operational sequence by monitoring the temperature signal from the temperature sensors 38 and by comparing the measured temperature with the desired predetermined temperature protocol, or time-temperature regimen, stored in the RAM 26. If the measured temperature indicates an undesired deviation has occurred or is anticipated, the computer 14 calculates a corrective strategy to achieve the predetermined temperature protocol. The computer 14 can, if desired, cause generation of an audible sound to alert the operator and request operator approval of the strategy. If the operator agrees with the proposed strategy, the operator enters the appropriate operator signal 31 by the keyboard 32. Alternatively, if the operator decides to override the suggestion of the computer 14, the operator enters the appropriate override operator signal 31 and generates the necessary replacement information to carry out a different schedule of energy input to achieve the predetermined temperature protocol, or regimen of time-temperature treatment. In another embodiment of the invention the system under control of the computer 14 can operate automatically without operator intervention except for emergency situations or for cases where the protocol is unable to achieve the anticipated treatment conditions.

There are also safety features for the hyperthermia treatment device, including an emergency shut off circuit which removes power to the energy applicator. The shut off circuit is activated if the operator does not respond within a reasonable time period to the prompt signal or if the temperatures reach dangerous levels. The system is able to save the treatment history information and after operator review of the treatment protocol and current history, the treatment can be resumed where it left off.

Figure 2:
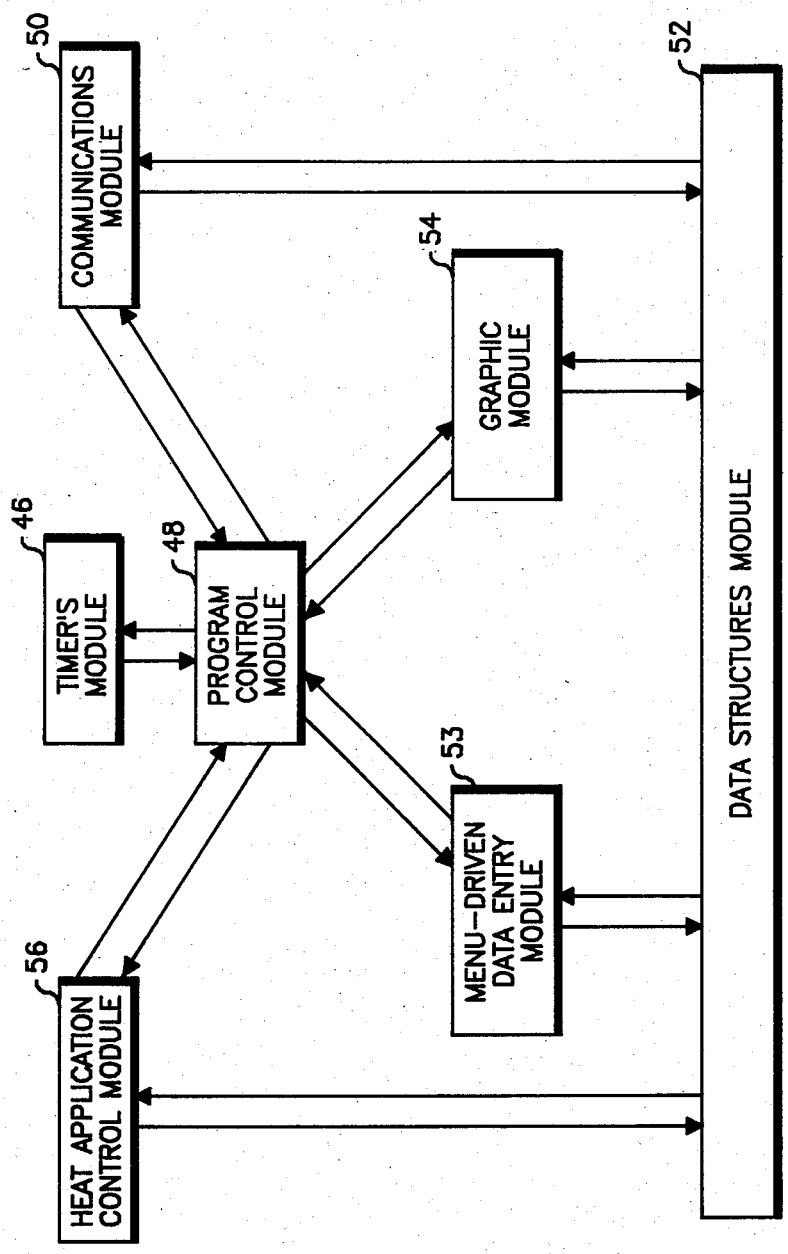
FIG. 2 is a functional block diagram showing the data flow among software programs (modules) for the hyperthermia treatment apparatus.

This monitoring and adjustment operation can be further explained by referring to FIG. 2 which illustrates data flow between the various computer software programs or modules. Many of these software programs comprise routines and operational sequences known to those of ordinary skill and are thus functionally explained herein. A program control module 48 is a supervisory type of software program linked with a timer module 46 and controls event, or interrupt, driven and/or program driven invocation of other software programs which are not involved with a data structures module 52. The data structures module 52 holds all the data needed by the various modules shown in FIG. 2, and is a passive module in that the program contains no executable code, only the data. The timer module 46 works with the program control module 48 and provides timing information for the invocation of program driven functions. A menu driven data entry module 53 is entirely program driven and obtains from the operator relevant information used to set temperature threshold levels, place the temperature sensors 38, activate the energy applicator and record the patient treatment history. A communications module 50 handles the transfer of the data and instructions between the computer 14 and the thermometry unit 36, the printer 29, the ultrasound energy controller 41 and the video display terminal 34. The communications module 50 incorporates both program and interrupt driven components. A graphics module 54 is program driven and performs all formatting and updating of the video display 42 for both temperature and energy level information. A energy or heat application control module 56 is program driven and operates on the temperature signal from the thermometry unit 36 to generate suggested strategies to the operator concerning adjustment of the ultrasound energy levels. The computer 14 interacts with other systems, such as for example, various ones of the modules, to monitor periodically the temperatures responsive to a timer program in the timer module 46. The timer module 46 utilizes a clock (not shown) which times out to actuate the program control module 48 and causes generation of a signal to the communications module 50. The communications program 50 in turn causes sampling of the temperature sensors 38, and the temperature information resides in a data structures module 52. The program control module 48 invokes the graphics module 54 which uses the temperature data in the data structure module 52 to update the video display 42. The graphics module 54 is program driven and includes the program listed in the Appendix which defines the image location and shape on the video display 42. The graphics module 54 also includes a vector graphics program to draw the images and is an off-the-shelf package, (CSP-2 provided by Peritek Corp., Oakland, Calif.).

During the hyperthermia treatment the operator therefore observes the updated condition of the correlative temperature data and responds by entering the operator signal 31 via the keyboard 32. The program control module 48 activates the energy applications module 56 to change the level of applied energy to attain the predetermined temperature protocol. This interactive process then periodically repeats itself to maintain control of the temperature.

In other embodiments of the invention the computer 14 can be programmed to generate at selected intervals a message on the video display terminal 34. This message can inform the operator of the time-temperature state of the temperature sensors 38 and display differences from the predetermined time-temperature protocol. For example, at periodic intervals the computer 14 can generate on the video display terminal 34 the sensor number, whether the temperature is from the tumor region or the normal tissue region, the elapsed time and temperature and the difference in temperature from the desired predetermined temperature protocol.

Figure 3B:
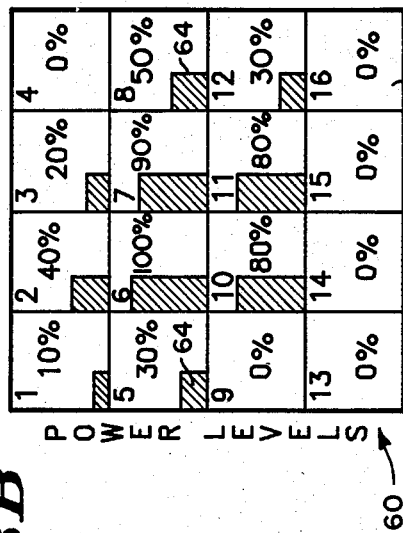
FIG. 3B illustrates a video presentation of a grid area corresponding to the area of FIG. 3A with each of sixteen indicated grid area elements capable of receiving selected percentages of energy from an applicator.
Figure 3A:
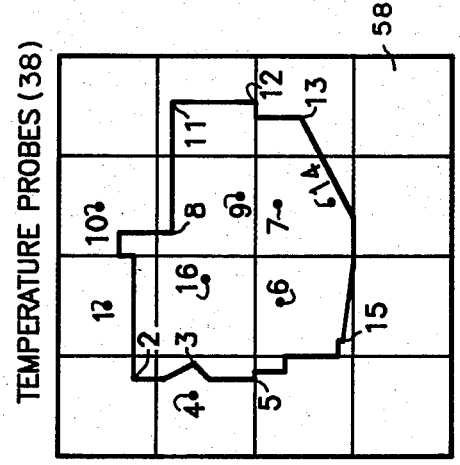
FIG. 3A illustrates a video presentation of a grid within which is delineated an outline of a tumor with the location of temperature sensors shown as numbers.
Figure 3C:
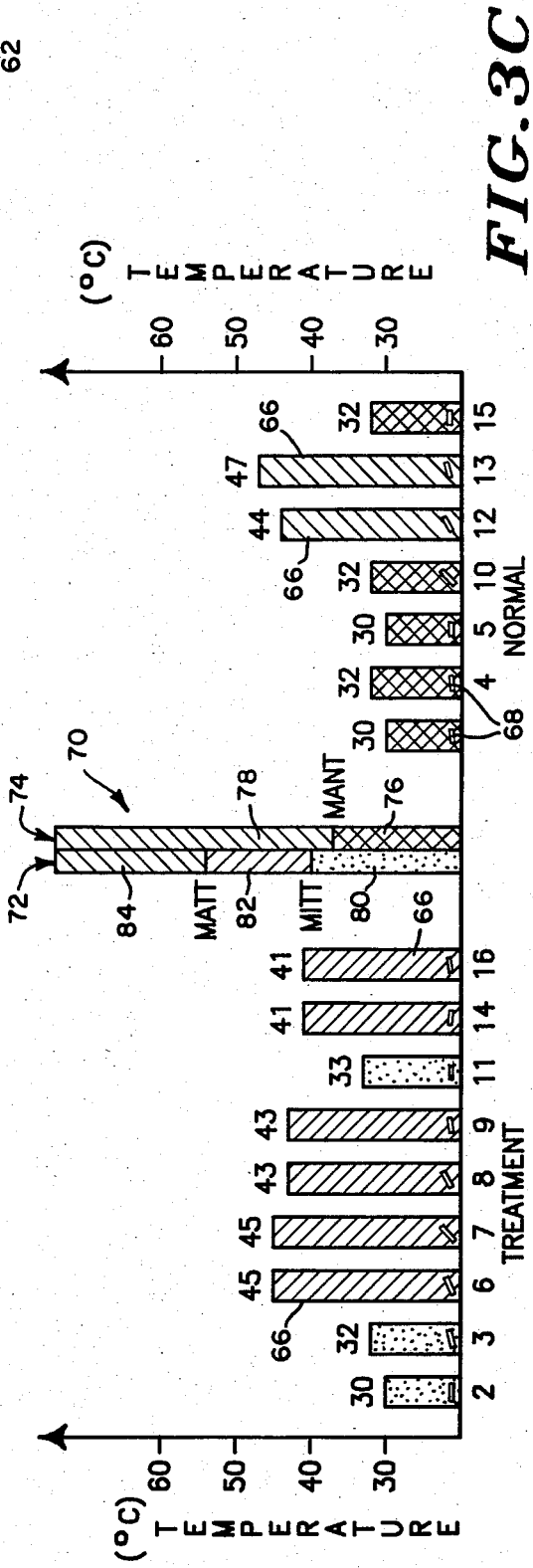
FIG. 3C illustrates a video presentation of selected temperature correlative data wherein predetermined temperature threshold zones are each associated with a preselected color.

The video display presentation of FIGS. 3A-C includes a variety of correlative temperature data which enables the operator to monitor and adjust the applied energy detected by the plurality of temperature sensors 38 in order to achieve the predetermined temperature protocol for optimum therapeutic effect. The operator begins the treatment procedure by placement of the temperature sensors 38 in the patient's body in the manner described hereinbefore. The spatial location of the tumor should already have been established with reasonable accuracy by other means, such as, x-ray radiography or fluoroscopy, or simply by sense of touch to isolate the tumor position if the tumor is near the skin surface. The relative spatial locations of the temperature sensors 38 and the tumor should be determined with good accuracy. The relative coordinates of the temperature sensors 38 are then entered by the keyboard 32, and the sensor coordinates are designated as within or outside the tumor region. These sensor coordinates are then illuminated on the video display 42 by placing the associated number of the sensor 38 at that location (shown as 1–16 in FIG. 3A). An outline of the tumor region is calculated from these sensor coordinates using a software program entered from either the floppy disk storage unit 22 or the Winchester storage unit 20. On the basis of the tumor area within each of the sixteen subelements 58 in the grid of FIG. 3A, another software program calculates the pattern of ultrasound energy which will be applied to the subelements 58 to heat the tumor region.

Initially, the energy applicator will generate ultrasound energy at the one hundred percent level because it is desirable to reach the optimum temperature threshold zone as quickly as possible to provide the optimum therapeutic result. Furthermore, rapid attainment of the desired treatment temperature minimizes treatment time for the patient and minimizes both equipment use time and the operator time per treatment cycle which contribute to a more efficient process and a more desirable treatment protocol. Once the temperatures begin to approach the desired temperature ranges, the power levels are reduced (as shown in FIG. 3B) to allow steady state, controlled treatment temperatures to be maintained. FIG. 3B illustrates another portion of the video presentation which shows a four-by-four array 60 which portrays the subdivision of energy application by the ultrasound applicator. Exemplary applied power or energy levels are indicated numerically in square subelements 62 of FIG. 3B, and the power level is also illustrated by colored bars 64 expandably positioned horizontally or vertically within each of the subelements 62. In other embodiments of the invention, the relative percentages of power can be indicated by a variable size, concentrically expanding square or circle positioned within the subelements 62.

The correlative temperature data of FIG. 3C includes vertically positioned bar graphs of the temperature at each of the associated temperature sensors 38 with the sensor number indicated at the bottom of each color coded bar 66. Preferably the selected color code comprises a plurality of different colors, but in other embodiments of the invention the plurality of colors becomes a plurality of grey scale values for one selected fundamental color.

The bar graph temperatures have been separated into two groups, one associated with therapeutic temperatures in the tumor region and another group associated with temperatures in normal tissue. Each of the color coded bars 66 also has a digital readout of the associated temperature positioned near the top of each of the bars 66. Toward the bottom of each of the bars 66 is an "icon" or indicator bar 68 which signifies the relative rate of temperature change for the associated temperature sensor 38. In the illustrated embodiment, there are five angular positions for the indicator bar 68, wherein a zero rate of temperature change is indicated by a horizontal position for the indicator bar. For non-zero temperature rates of change, there are two angular positions tilted upward and two positions tilted downward from the horizontal position which are indicative, respectively, of increasing and decreasing rates of temperature change. In other embodiments of the invention, the rates of temperature change can be indicated by continuously variable positions for the indicator bar 68, or by an expanding pie-shaped section or by a concentrically expanding circular or square area disposed within or associated with each of the color coded bars 66.

The two groups of temperature bar graphs shown in FIG. 3C are separated from one another by a color coded temperature threshold scale 70, and the scale 70 itself is divided into a first vertical portion 72 for the treatment, or tumor, region and a second vertical portion 74 associated with the normal tissue region. The second vertical portion 74 for the normal tissue region is divided into two temperature threshold zones of preselected colors, wherein the colors representing the predetermined temperature threshold zones are changeable by the operator specifying the limits of the zones, preferably at startup of the treatment. The two zones for the normal time region are: (1) a safe zone 76 having an upper threshold MANT (maximum allowed normal temperature), and in this safe zone 76, normal tissue is substantially unharmed by the treatment, and (2) a harmful zone 78 above the threshold value MANT wherein normal tissue suffers increasing damage as the temperature increases. These two zones can also be referred to as a desirable zone and an undesirable zone, respectively. The first vertical portion 72 for the tumor region is divided into three temperature threshold zones of preselected colors, and the zone limits are determined by the operator, again preferably at startup: (1) a lower zone 80 wherein tumor tissue is not normally affected, (2) a preferred temperature treatment zone 82 having a lower threshold temperature of MITT (minimum treatment temperature) and an upper threshold temperature of MATT (maximum treatment temperature), and within the zone 82 the tumor tissue degrades, and (3) an upper zone 84 above the MATT threshold temperature, and within the zone 84 tumor degradation is not nearly as pronounced as in the preferred zone 82 and can result in excessive damage to surrounding normal tissue. In the case of breast tumors, for example, the threshold temperatures values include a value of about 40° C. for the MANT, the MITT is approximately 42.5° C. and the MATT is about 48° C. These three zones can also be divided into the desirable zone (the zone 82) and the undesirable zone (the zones 80 and 84). It should also be noted that the positioning of these threshold temperatures is somewhat flexible because the hyperthermia treatment is actually a time-temperature treatment such that substantially the same thermal result can be obtained for long term treatments at lower temperatures and for short term treatments at higher temperatures. Therefore, the above threshold temperatures are nominal values which can be adjusted somewhat depending on the treatment time.

By observing this collective temperature data the operator is able to monitor numerous variables in an efficient manner, including the rate of change of temperature with time, the temperatures of the tumor region and normal tissue region and whether or not the temperature of each of the temperature sensors 38, and each group of sensors, is in the optimum temperature threshold zone. Furthermore, FIG. 3A simultaneously displays the spatial location of the temperature sensors 38 with respect to the tumor, and each of the sensor numbers is color coded to the temperature threshold scale 70, enabling correlation of spatial location to the ongoing therapeutic effectiveness of the temperature at that location.

The time history of the temperature correlative data displayed in FIGS. 3A-C is preferably stored in the Winchester storage unit 20 or in the floppy disk storage unit 22. This information is also added to the past history of the patient in order to assess treatment progress and prognosis. The temperature correlative data and the associated therapeutic result are also stored in one of the storage means for purposes of accumulating a general data base of treatment response to obtain statistically meaningful information for developing the optimum treatment protocol for a wide range of tumor sizes, locations and classes or types (stage of growth). Therefore, a particular protocol can be prepared by mapping data in the data base to determine tumor characteristics corresponding to the tumor in the patient's body. The protocol in the data base can then be modified to account for differences between the patient and data base tumors to provide the predetermined treatment protocol for the patient.

In a typical hyperthermia treatment procedure, the correlative temperature data for each set of the temperature sensors 38 shown in FIG. 3 is updated approximately every fifteen to thirty seconds during the startup portion of the treatment due to the reasonably large rate of temperature increase. The frequency of the updating at any time also depends on individual characteristics of the anatomical site of the tumor, such as proximity to bones or other structures which affect energy absorption in the vicinity of the tumor. Once the temperature approaches the desired steady state level, the correlative temperature data of FIG. 3 is typically updated approximately every two to four minutes since temperature changes occur quite slowly for most treatment conditions. Again however, it should be noted that for treatment of tumors which are closely positioned to bone structure or other masses which preferentially reflect ultrasound energy, the update should be done more frequently. Similarly if one is using microwave energy, fatty tissue preferentially absorbs microwaves and thus necessitates frequent temperature update. For situations which require only occasional update of the correlative temperature data, the computer 14 is able to devote itself to data analysis and generation of information useful to the diagnostician. Therefore, in one form of the invention the accumulated patient response can be compared with the general treatment data base to analyze trends in treatment and if necessary prepare a modified form of the predetermined treatment protocol. For example, the ongoing real time patient response can be modified in view of an unexpected patient response, such as unpredicted preferential ultrasound energy reflection by a nearby bone structure.

In another embodiment of the invention, the computer 14 can utilize the time-temperature history to prepare color coded topographical maps of isothermal treatment regions as a function of time and of spatial location within and near the tumor. By using a plurality of the temperature sensors 38 inserted along a series of depth positions in the tumor, a three dimensional set of temperatures can efficiently be collected, and an expanded grid of interpolated temperature can be calculated. A three dimensional form of the topographical maps is then constructed from a set of two dimensional parallel slices. By appropriate positioning of the temperature sensors 38 and by performing suitable interpolations, the topographical maps can be constructed for planar sections perpendicular to any one of three possible dimensions. The resulting topographical maps are viewable one at a time or can be displayed dynamically to view the evolution of the treatment protocol throughout the treatment period.

Figure 4:
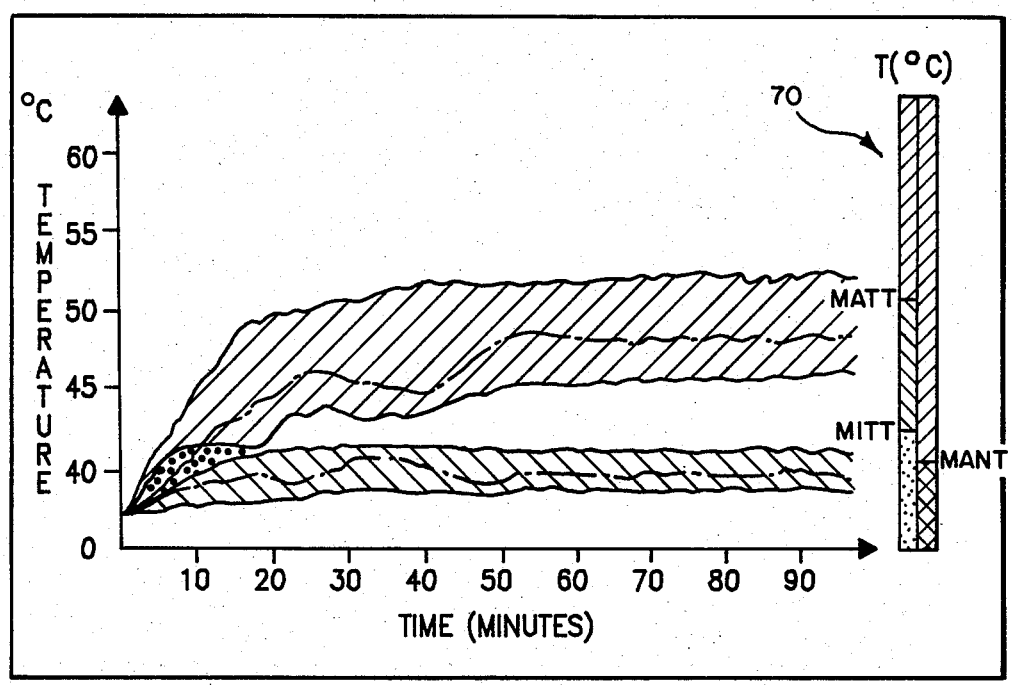
FIG. 4 illustrates a video presentation of the time-temperature history of minimum and maximum temperatures attained among temperature sensors within each of the two groups of sensors in the tumor region and in the normal tissue region.

Additional time-temperature history information is obtainable from the video presentation shown in FIG. 4. This shows the maximum and minimum range of temperatures reached among all of the temperature sensors 38 in each of the two groups of sensors, one group associated with the treatment region and the other group associated with the normal tissue region. An average temperature is also calculated for each group and is a single bold dashed line appearing within the range of values in each of the plots for the two groups. Also included in the display for comparison purposes is the color coded temperature scale 70 used in FIG. 3C to indicate the various temperature threshold zones. The operator is therefore able to correlate the range of the minimum and maximum temperature values, the time-temperature integrated areas which lie within and which exceed the various temperature threshold zones and the behavior of the average temperature value with respect to these temperature threshold zones.

Information from the video presentation can be used as a basis for various figures of merit to evaluate therapeutic effectiveness of treatments, such as for example, by comparing the relative magnitude of time-temperature integrated areas within and outside of the temperature threshold zones. Generally, the term comparing is meant to include at least calculation of ratios and arithmetic differences and various selected powers of these quantities, such as the square and square root thereof. These figures of merit can also be used to characterize a data base of use in planning future treatments and to adapt ongoing treatments to obtain more effective treatment results. The amount of deviation from the planned protocol can be another measure of the figure of merit. An additional useful figure of merit is the degree of overlap of the ranges of temperature for the two groups of sensors. This overlap is the dotted area in FIG. 4, and the comparison of the integrated area of the dotted region relative to the total area within the range curves can be used as a figure of merit for evaluating the effectiveness of the treatment. Another figure of merit relates to the comparison of the overlap area with the total area which is time bounded by the startup of the hyperthermia treatment and by the end of the overlap area. Additional figures of merit arise from, for example, comparison of selected areas of this time bounded region which also fall within selected ones of the temperature threshold zones. Further, the treatment protocol, the various figures of merit and the therapeutic results can be stored to accumulate a data base and can be compared with patient response and with other data bases to adjust treatment conditions to improve ongoing, as well as future treatments.

In other embodiments of the invention, other figures of merit can be obtained by determining the percentage of time the temperatures of each of the temperature sensors fall within selected ones of the temperature threshold zones. For example, comparing the relative percentages of time within the desirable and the undesirable zones can yield a figure of merit for evaluating the effectiveness of a particular treatment protocol. Thus, the greater the percentage of time in the desirable zones, the more favorable is the figure of merit.

Figure 5:
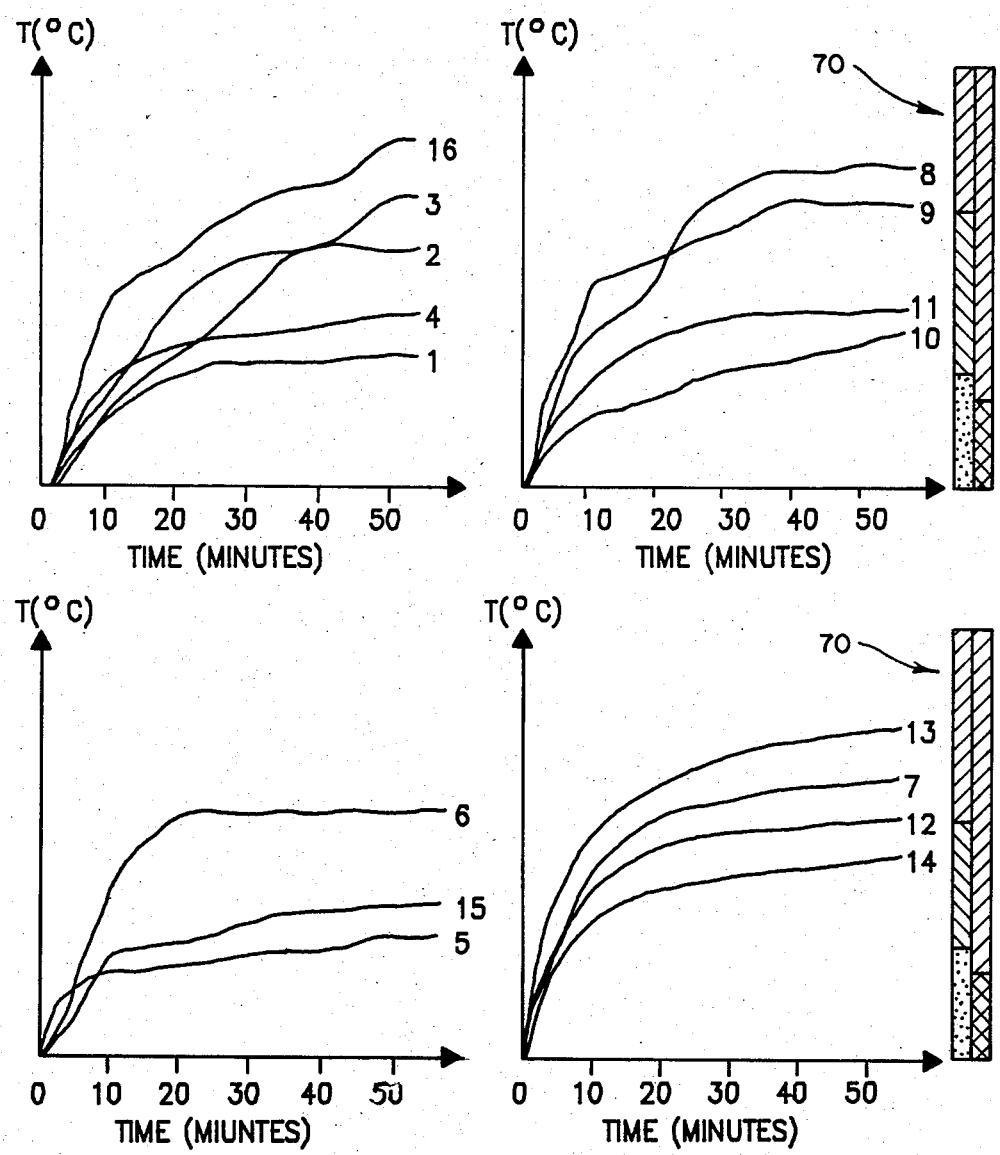
FIG. 5 illustrates a video presentation of the time-temperature history for the temperature sensors positioned within the associated four quadrants of the grid shown in FIG. 3A.

The time-dependent temperature data history of each of the temperature sensors 38 can also be followed by the video presentation portrayed in FIG. 5. The time-temperature data for the sensors 38 located in each of the four rectangular quadrants of FIG. 3A can be included in one video presentation with four plots displayed, each plot congruently associated with its respective quadrant in FIG. 3A. Also included in the figure is the color coded scale 70 of FIG. 3C for comparison of temperature values with the various temperature threshold zones. In another embodiment of the invention, if the sensors 38 are concentrated, for example, in only one or two of the four quadrants, the array of temperature sensors 38 is divided into the four individual plots of FIG. 5 by repositioning the center of the quadrants at approximately the center of gravity of the clustered sensor locations. For the temperature sensors 38 in the repositioned quadrants, the time-temperature plots are generated for analysis by the operator.

Figure 6:
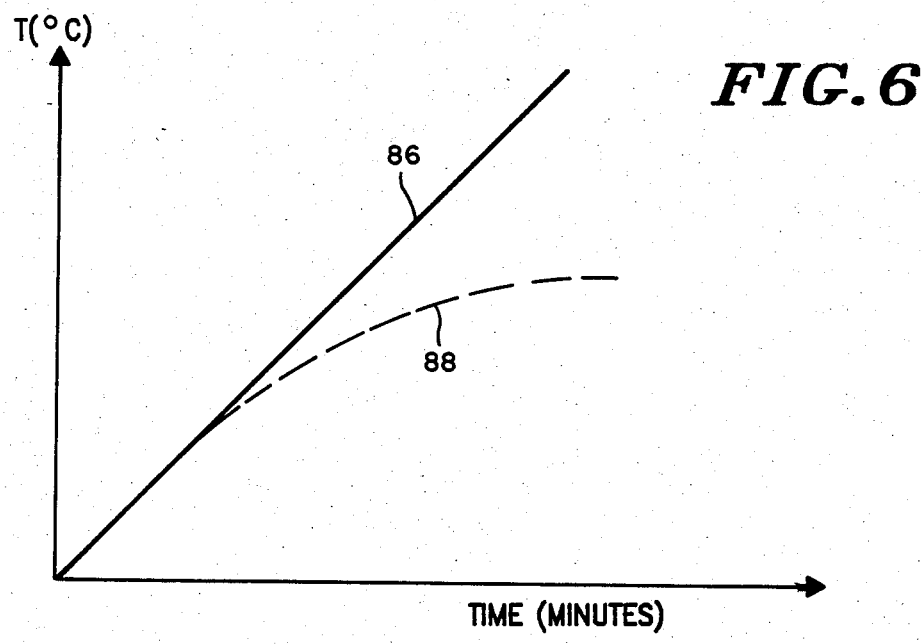
FIG. 6 illustrates the functional dependence of a linear and a typical non-linear time-temperature dependent function used to predict treatment temperature at a future time.

Control of energy input by the ultrasound applicator 12 involves use of computer software composed of selected polynomial and transcendental functions to predict the temperature at a future time given the past shape of a measured time-temperature curve. The nature of the function most useful under any particular treatment conditions depends on numerous variables such as, for example, tissue makeup, proximity to bone structure and blood flow rates. Consequently, in one embodiment of the invention, a plurality of functions can be made available in the form of computer software programs for fitting measured hyperthermia treatment temperatures and for carrying out selected statistical evaluations, such as least squares fits, to ascertain the most appropriate function to use for predicting temperature at a future time in the treatment. Selection of functions can also be changed for different regimes of the treatment protocol. For example, in the starting phase of the hyperthermia treatment, the functional behavior will more likely be a quasi-linear behavior as for a first curve 86 shown in FIG. 6, but as the temperature approaches a steady state value, the functional form can assume, for example, a more exponential shape, such as a second curve 88 in FIG. 6. The operator will be able to call upon the previously mentioned time-temperature dependent general data base in order to isolate during the treatment the most probable function of use in predicting changes in temperature for selected characteristic tumor conditions.

What is claimed is:

1. A system for controlling a hyperthermia treatment device of the type which has applicator means for applying energy to attain a predetermined temperature protocol for portions of a patient's body, the system monitoring said energy application and being capable of adjusting said energy application responsive to operator manipulation, said system comprising:
    means for sensing temperature of the patient's body and for providing a temperature signal;
    computer means having associated instruction and data storage means for interacting with other systems means to perform the energy application, said computer means monitoring said temperature signal and adjusting said energy application responsive to the operator manipulation and having data and instructions defining said predetermined temperature protocol, said computer means utilizing said temperature signal and said protocol defining data and instructions to selectively provide an operator prompt signal indicating the desirability of the operator adjusting said energy application and further providing correlative temperature data associated with said portions of the patient's body;

operator means responsive to the operator manipulation for providing an operator signal to control said energy applicator means via said computer means; and means responsive to said correlative data and said protocol defining data and instructions for displaying a video presentation of said correlative temperature data to the operator, said correlative temperature data displayed in a color coded manner such that preselected colors represent predetermined temperature effectiveness zones of hyperthermia treatment, the operator capable of adjusting said energy application by evaluating said color coded video presentation and providing said operator signal.

2. The system as defined in claim 1 wherein said operator means comprises a remote interaction device.

3. The system as defined in claim 1 wherein said applicator means comprises an ultrasound energy applicator.

4. The system as defined in claim 1 wherein said correlative temperature data comprises selectively at least one of temperature data from (a) a group of said sensing means inside a tumor region, (b) a group of said sensing means outside said tumor region, (c) a mixture of groups from inside and outside said tumor region, (d) a group of said temperature sensing means within said preselected subelement wherein said system is adapted to control the temperature, and (e) a group of said temperature sensing means within and without each said preselected subelement wherein said system is adapted to control the temperature.

5. The system as defined in claim 1 wherein said video presentation comprises at least one of (a) a grid display illustrating subelement areas therein and further showing locations of said temperature sensing means with respect to said tumor and said locations depicted using said preselected color and (b) a bar graph in each said subelement area depicting power level input to each said subelement area.

6. The system as defined in claim 1 wherein said prompt signal comprises time-temperature state information displayed periodically with time.

7. The system as defined in claim 6 wherein said time-temperature state information comprises selectively a temperature sensor number, a digital temperature value, elapsed time and temperature difference from the temperature of said predetermined temperature protocol.

8. The system as defined in claim 1 wherein said correlative temperature data comprises means for showing time rate of temperature increase for each said temperature sensing means.

9. A system for controlling a hyperthermia treatment device applicator means for applying energy to attain a predetermined temperature protocol for treating a tumor in a portion of a patient's body, the system cooperating with an operator to monitor and adjust said energy to achieve said protocol, said system comprising:

computer means for controlling said applicator means and coupled to operator means, temperature sensing means, video output means and alphanumeric output means;

operator means responsive to an operator input for providing an operator signal to control said applied energy to achieve said predetermined temperature protocol;

temperature sensing means for providing a temperature sensor signal to said computer means, said computer means utilizing said sensor signal and data and instructions characteristic of said predetermined temperature protocol and selectively providing a prompt signal requesting adjustment of said energy by the operator and further providing correlative temperature data associated with said portions of the patient's body;

means for providing a video output responsive to said correlative temperature data;

means for providing an alphanumeric output responsive to said prompt signal; and means responsive to said video output for displaying a video presentation to the operator of said correlative temperature data, said correlative temperature data displayable using a plurality of colors wherein each said color corresponds to predetermined temperature threshold zones of hyperthermia treatment and the operator responding to said request for energy adjustment by evaluating said video presentation and providing said operator signal.

10. The system as defined in claim 9 wherein said operator means comprises a remote interaction device.

11. The system as defined in claim 9 wherein said computer means utilizes said sensor signal and said preselected temperature protocol by comparing amplitudes of said sensor signal and said preselected temperature protocol.

12. The system as defined in claim 9 wherein said video presentation further includes a grid display illustrating location with respect to said tumor of said temperature sensing means, said temperature sensing means displayable using said plurality of colors corresponding to said threshold zones.

13. The system as defined in claim 9 wherein said temperature sensing means comprises a thermocouple disposed within said patient's body.

14. The system as defined in claim 9 wherein said temperature sensing means comprises a thermistor.

15. The system as defined in claim 9 wherein said video presentation comprises at least one of (a) a grid display illustrating subelement areas therein and further showing locations of said temperature sensing means with respect to said tumor and said locations depicted using said preselected color and (b) a bar graph in each said subelement area depicting power level input to each said subelement area.

16. The system as defined in claim 9 wherein said prompt signal comprises time-temperature state information displayed periodically with time.

17. The system as defined in claim 16 wherein said time-temperature state information comprises selectively a temperature sensor number, a digital temperature value, elapsed time and temperature difference from the temperature of said predetermined temperature protocol.

18. The system as defined in claim 9 where said plurality of colors comprises a plurality of grey scale values for one fundamental color.

19. The system as defined in claim 9 wherein said correlative temperature data comprises means for showing time rate of temperature increase for each said temperature sensing means.

20. A method for preparing a predetermined hyperthermia treatment protocol for a tumor in a portion of a patient's body using a hyperthermia treatment data base defining a plurality of general hyperthermia treatment protocols, comprising the steps of:
   identifying location, size and type characteristics of said tumor in the patient's body;
   mapping data in said hyperthermia treatment data base corresponding to tumor characteristics identified in said patient's body; and
   modifying a selected one of said general hyperthermia treatment protocols for said tumor to account for said identified location, size and type characteristics of said tumor in said patient's body to develop said predetermined hyperthermia treatment protocol.

21. A method under control of a computer and manipulated by an operator using a predetermined temperature protocol for accumulating a hyperthermia treatment data base for tumors in specific portions of a patient's body, comprising the steps of:
   (a) applying energy to heat said portions of the patient's body;
   (b) sensing temperatures in said portions of the patient's body;
   (c) comparing said sensed temperature with temperature from said predetermined temperature protocol;
   (d) selectively generating a prompt signal for observation by said operator requesting adjustment of said energy, said prompt signal generated responsive to said step of comparing, indicating a deviation from said predetermined temperature protocol;
   (e) generating correlative temperature data associated with said portions of the patient's body;
   (f) generating a video output responsive to said correlative temperature data;
   (g) displaying a video presentation to said operator responsive to said video output, said video presentation displayable using a plurality of colors wherein each of said colors corresponds to a preselected temperature threshold zone, and said operator responding to said prompt signal by evaluating said video presentation and providing an operator signal to attain said predetermined temperature protocol;
   (h) storing said correlative temperature data in storage means; and
   repeating steps (a)-(h) until completion of said predetermined temperature protocol and completion of said storing of said correlative temperature data.

22. The method of claim 21 further including the steps of storing treatment effect of said predetermined temperature protocol in said storage means in association with said protocol.

23. A method for establishing a hyperthermia treatment data base useful for preparing a predetermined hyperthermia treatment protocol for therapeutic treatment of tumors in specified portions of a patient's body, comprising the steps of:
   performing a planned patient hyperthermia treatment protocol by applying energy to heat said portions of the patient's body;
   measuring time dependent temperature data for said hyperthermia treatment protocol;
   storing said time dependent temperature data in a storage means;
   calculating a figure of merit from said time dependent temperature data;
   determining treatment effect of said hyperthermia treatment protocol; and
   storing said treatment effect and said figure of merit in said storage means in association with said time dependent temperature data.

24. The method as defined in claim 23 wherein said step of calculating a figure of merit comprises determination of a deviation of said measured time dependent temperature data from said planned treatment protocol.

25. A method of determining a figure of merit for use in evaluating a hyperthermia treatment of a tumor in a portion of a patient's body using an apparatus having a group of temperature sensors disposed in the tumor and another group of temperature sensors disposed in surrounding normal tissue, comprising:
   applying energy to heat said portion of the patient's body;
   sensing temperatures by said group of temperature sensors disposed in said tumor and by said group in said surrounding normal tissue;
   determining periodically throughout said hyperthermia treatment a minimum and maximum temperature range for said group of temperature sensors disposed in said tumor and for said group in said surrounding normal tissue;
   calculating a time-temperature integrated overlap of said minimum and maximum temperature ranges for each of said groups of temperature sensors;
   calculating a time-temperature integrated area for said temperature range for each said group of temperature sensors; and
   determining a percentage for said integrated overlap and for said integrated area, said determined percentages compared arithmetically to characterize said figure of merit.

26. The method as defined in claim 25 wherein said integrated area comprises a total area for said hyperthermia treatment within said temperature range for each said group.

27. The method as defined in claim 25 further including the step of assigning temperature threshold zones for each of said groups of temperature sensors, said integrated areas for each said group comprising an area of said temperature range which lies within selected ones of said temperature threshold zones.

28. The method as defined in claim 27 wherein said areas within said temperature threshold zones are time bounded by startup of said hyperthermia treatment and by the end of said integrated overlap.

29. A method of determining a figure of merit for use in evaluating a hyperthermia treatment of a tumor in a portion of a patient's body using an apparatus having a group of temperature sensors disposed in the tumor and another group of temperature sensors disposed in surrounding normal tissue, comprising the steps of:
   applying energy to heat said portion of the patient's body;
   sensing temperatures by said group of temperature sensors disposed in said tumor and said group in said surrounding normal tissue;
   determining periodically throughout said hyperthermia treatment a minimum and maximum temperature range for said group of temperature sensors disposed in said tumor and for said group in said surrounding normal tissue;

assigning temperature threshold zones for each of said two groups of temperature sensors;

determining time-temperature integrated areas which lie within and which exceed said temperature threshold zones; and comparing arithmetic relative percentages of said integrated areas which lie within said temperature threshold zones with said integrated areas which exceed said temperature threshold zones, said arithmetic relative percentages characteristic of said figure of merit.

30. The method as defined in claim 29 wherein said step of comparing arithmetic percentages comprises calculating a difference of said percentages.

31. The method as defined in claim 29 wherein said step of comparing arithmetic percentages comprises calculating a ratio of said percentages.

32. A method of determining a figure of merit for use in evaluating a hyperthermia treatment of a tumor in a portion of a patient's body using an apparatus having a group of temperature sensors disposed in the tumor and another group of temperature sensors disposed in surrounding normal tissue, comprising the steps of:

applying energy to heat said portion of the patient's body;

sensing temperatures by said group of temperature sensors disposed within said tumor and in said surrounding normal tissue;

determining periodically throughout said hyperthermia treatment a minimum and maximum temperature range for said group of temperature sensors disposed in said tumor and for said group of temperature sensors in said surrounding normal tissue;

assigning temperature threshold zones for each of said two groups of temperature sensors;

determining time-temperature integrated areas which lie within and which exceed said temperature threshold zones; and comparing arithmetic relative percentages of said integrated areas which lie within said temperature threshold zone with said integrated areas which exceed said temperature threshold zones, said relative percentages being characteristic of said figure of merit.

33. The method as defined in claim 32 further including the step of adjusting said applied energy to improve said figure of merit during said hyperthermia treatment.

34. A method for generating a topographical display of temperature isotherms in a set of planes of a patient's body for a hyperthermia treatment of a tumor in a portion of said patient's body, comprising the steps of:

applying energy to said portion of the patient's body;

sensing temperatures in said portion of said patient's body;

generating an interpolated set of temperatures for said set of planes from said sensed temperatures;

assigning color codes to said temperature isotherms of said set of planes, each said color code corresponding to predetermined temperature effectiveness zones of hyperthermia treatment for said patient's body portion; and generating said topographical display of said temperature isotherms in said set of planes of the patient's body.

35. A method of determining figures of merit for use in a hyperthermia treatment of a tumor in a portion of a patient's body using an apparatus having a group of temperature sensors disposed in the tumor and another group of temperature sensors disposed in surrounding normal tissue, comprising the steps of;

applying energy to heat said portion of the patient's body;

sensing temperatures periodically throughout said hyperthermia treatment for said group of temperature sensors disposed in said tumor and said group in said surrounding normal tissue;

storing in storage means said sensed temperatures for each said group of temperature sensors;

assigning a temperature threshold zone to each said sensed temperatures;

determining percentages for each said group of said sensed temperatures which lie within each said temperature threshold zone; and calculating said figures of merit by comparing selected ones of said determined percentages associated with said temperature threshold zones.

36. The method as defined in claim 35 wherein said temperature threshold zones comprise a desirable and an undesirable zone for each said group of temperature sensors, said figure of merit characterized by comparing of said percentages of said sensed temperatures associated with said desirable zones and with said undesirable zones.

37. The method as defined in claim 36 wherein said comparing of said percentages comprises calculating for each said group of sensors a ratio of said percentages associated with said desirable zones to said percentage associated with said undesirable zones.

38. The method as defined in claim 36 wherein said undesirable zone for said group of temperature sensors in the tumor comprises a lower zone and an upper zone and said undesirable zone for said group of temperature sensors in the normal tissue comprises a harmful zone.

39. The method as defined in claim 35 further including the step of adjusting said applied energy to improve said figure of merit during said hyperthermia treatment.

40. A hyperthermia system for achieving a predetermined temperature protocol for a portion of a patient's body, the system monitoring energy application to the patient body portion and adapted for adjusting said energy application responsive selectively to operator manipulation and computer control, comprising:

means for applying energy to the patient body portion, said energy applying means having subelement energy applicators providing energy to preselected subelements of the patient body portion;

means for sensing temperature of the patient body portion and for providing temperature signals characteristic of the patient body portion;

computer means, having associated means for storing instructions and data defining said predetermined temperature protocol, for interacting with the other parts of said system to perform said energy application, said computer means monitoring said temperature signals from the patient body portion and adjusting said energy application to said subelement energy applicators responsive selectively to said computer means providing said instructions and data defining said predetermined temperature protocol and to the operator manipulation, and said computer means utilizing said temperature signals and said instructions and data to selectively provide an operator prompt signal indicating the desirability of the system operator adjusting said energy application, said computer means further providing correlative temperature data associated with said patient body portion; and operator means responsive to the operator manipulation for providing an operator signal to control said energy applying means via said computer means.

41. The system as defined in claim 40 wherein said correlative temperature data comprises selectively at least one of temperature data from (a) a group of said sensing means inside a tumor region, (b) a group of said sensing means outside said tumor region, (c) a mixture of groups from inside and outside said tumor region, (d) a group of said temperature sensing means within said preselected subelement wherein said system is adapted to control the temperature and (e) a group of said temperature sensing means within and without each said preselected subelement wherein said system is adapted to control the temperature.

42. A hyperthermia system for achieving a predetermined temperature protocol for a portion of a patient's body, the system monitoring energy application to the patient body portion and adapted for adjusting said energy application responsive selectively to operator manipulation and computer control, comprising:
    means for applying energy to the patient body portion, said energy applying means having subelement energy applicators providing energy to preselected subelements of the patient body portion;
    means for sensing temperature of the patient body portion and for providing temperature signals characteristic of the patient body portion;
    computer means, having associated means for storing instructions and data defining said predetermined temperature protocol, for interacting with the other parts of said system to perform said energy application, said computer means monitoring said temperature signals from the patient body portion and adjusting said energy application to said subelement energy applicators responsive selectively to said computer means providing said instructions and data defining said predetermined temperature protocol and to the operator manipulation, and said computer means utilizing said temperature signals and said instructions and data to selectively provide an operator prompt signal indicating the desirability of the system operator adjusting said energy application, said computer means further providing correlative temperature data associated with said patient body portion; and
    operator means responsive to the operator manipulation for providing an operator signal to control selectively each said subelement energy applicator of said energy applying means via said computer means.

43. The system as defined in claim 42 wherein said correlative temperature data comprises selectively at least one of temperature data from (a) a group of said sensing means inside a tumor region, (b) a group of said sensing means outside said tumor region, (c) a mixture of groups from inside and outside said tumor region, (d) a group of said temperature sensing means within said preselected subelement wherein said system is adapted to control the temperature and (e) a group of said temperature sensing means within and without each said preselected subelement wherein said system is adapted to control the temperature.

44. The system as defined in claim 42 further including means responsive to said instructions and data for displaying a video presentation of said correlative temperature data to the operator and displayable in a color coded manner such that preselected colors represent predetermined temperature effectiveness zones of hyperthermia treatment, the operator capable of adjusting the energy application by evaluating said color coded video presentation and providing said operator signal.

45. A hyperthermia system for achieving a predetermined temperature protocol for a portion of a patient's body, the system monitoring energy application and adapted for adjusting said energy application responsive selectively to operator manipulation and computer control, comprising:
    means for applying energy to preselected subelements of the patient body portion;
    means for sensing temperature at a plurality of locations in said patient body portion;
    computer means, having associated means for storing instructions and data defining said predetermined temperature protocol, for interacting with other parts of said system to perform said energy application, said computer means monitoring said temperature signals from the patient body portion and adjusting said subelement energy application responsive selectively to said computer means providing said instructions and data defining said predetermined temperature protocol and to the operator manipulation, and said computer means providing correlative temperature data from said temperature signals from said plurality of locations and enabling selectively at least one of said computer means and the system operator to adjust said energy application for each said preselected subelement of said patient body portion responsive to evaluating said temperature signals from selectable ones of said patient body portion subelements.

46. The system as defined in claim 45 wherein said correlative temperature data comprises means for showing time rate of temperature increase for each said temperature sensing means.

* * * * *